United States Patent [19]

Spilburg et al.

[11] 4,243,582

[45] Jan. 6, 1981

[54] NOVEL GLYCOPROTEINS FROM BOVINE CARTILAGE

[75] Inventors: Curtis A. Spilburg, St. Louis; James M. Schuck, Chesterfield, both of Mo.

[73] Assignee: Monsanto Company, St. Louis, Mo.

[21] Appl. No.: 33,346

[22] Filed: Apr. 26, 1979

[51] Int. Cl.³ .............................................. C07G 7/00
[52] U.S. Cl. .................................. 260/112 R; 424/95; 424/177
[58] Field of Search .............. 260/112 R; 424/95, 177

[56] References Cited

U.S. PATENT DOCUMENTS

| | | | |
|---|---|---|---|
| 4,002,572 | 1/1977 | te Nijenhuis | 252/99 |
| 4,042,457 | 8/1977 | Kuettner et al. | 424/95 |
| 4,108,849 | 8/1978 | Thomas | 260/112 R |
| 4,154,821 | 5/1979 | Drouet et al. | 260/112 R X |
| 4,190,573 | 2/1980 | Zwisler et al. | 260/122 R |

OTHER PUBLICATIONS

Kuettner et al., *Experientia,* vol. 30, pp. 595-597 (1974).
Keuttner et al., *Biochem Biophys. Res. Comm.,* vol. 72, No. 1, pp. 40-46 (1976).
Langer et al., *Science,* vol. 193 (1976), pp. 70-72.

*Primary Examiner*—Howard E. Schain
*Attorney, Agent, or Firm*—Scott J. Meyer; James W. Williams, Jr.

[57] ABSTRACT

Two high purity glycoprotein components each having a molecular weight of about 65,000 daltons and having activity as trypsin inhibitors and inhibitors of endothelial cell growth are obtained from bovine cartilage extract. A guanidine hydrochloride extract of bovine cartilage is subjected to ammonium sulfate salt fractionation, DEAE-Sephadex ion exchange chromatography, SP-Sephadex ion exchange chromatography and Con A-Sepharose affinity chromatography to isolate these glycoproteins in a high purity preparation.

3 Claims, 2 Drawing Figures

NOVEL GLYCOPROTEINS FROM BOVINE CARTILAGE

BACKGROUND OF THE INVENTION

This invention relates to novel high purity glycoproteins having activity as trypsin inhibitors and inhibitors of endothelial cell growth.

It is known that proteinase inhibitors are widely distributed in animal tissues and body fluids. Some of these inhibitors have been suggested as important mediators of proliferative and invasive processes which affect developing or diseased tissues.

In particular, various cartilaginous and other such connective tissues have been described heretofore as sources of proteinase inhibitors. Kuettner et al, *Experientia* 30, 595-7 (1974). Subsequently, Kuettner et al, *Biochem. Biophys. Res. Comm.* 72 (1), 40-6 (1976), disclosed the isolation of a specific cationic trypsin inhibitor having a molecular weight of about 11,000. The material was derived from bovine cartilage by guanidinium hydrochloride extraction, ultrafiltration and Sephadex ® G-75 chromatography.

In another report from the foregoing investigators, trypsin inhibitors having molecular weights of 12,300 and 11,500 were reported to be isolated from bovine cartilage and aorta, respectively. Sorgente et al, *Protides of Biol. Fluids, Proc. Colloq.* 23, 227-30 (1976). The latter two inhibitors were obtained by extraction with guanidinium chloride and 2-(N-morpholino)-ethanesulfonic acid followed by dialysis, Sephadex CM-50 cation exchange, gel exclusion and affinity chromatography on insolubilized trypsin.

In U.S. Pat. No. 4,042,457, Kuettner et al, disclose the preparation of inhibitor substances from cartilage and other connective tissues having molecular weights below about 50,000. The materials are said to be effective for inhibiting cell proliferation and tissue invasion. In still another paper by these investigators, Eisenstein et al, *Amer. J. Path.* 81, 337-48 (1975), it is stated that the cartilage material having a molecular weight of 50,000 or above had no inhibitory effect on growth of endothelial cells in doses as high as 500 μg/ml.

Another group of investigators, Langer et al., *Science* 193, 80-2 (1976), disclosed the preparation of a cartilage factor having a molecular weight between about 14,400 and 17,800 which was shown to have trypsin inhibitory activity and activity that inhibits tumor neovascularization.

BRIEF DESCRIPTION OF THE INVENTION

In accordance with the present invention, two novel high purity glycoprotein components each having a molecular weight of about 65,000 are obtained from bovine cartilage extract. A guanidine hydrochloride extract of bovine cartilage is subjected to ammonium sulfate salt fractionation, DEAE-Sephadex ® ion exchange chromatography, SP-Sephadex ® ion exchange chromatography and Con A-Sepharose ® affinity chromatography to isolate these glycoproteins in a high purity preparation. The isolated glycoprotein components have activity as trypsin inhibitors and inhibitors of endothelial cell growth. These activities were unexpected in view of the aforesaid prior art on cartilage material which showed inhibitor activity at 11-12,000 molecular weights and lack of activity at about 50,000 molecular weight.

DETAILED DESCRIPTION OF THE INVENTION

Figure 1:
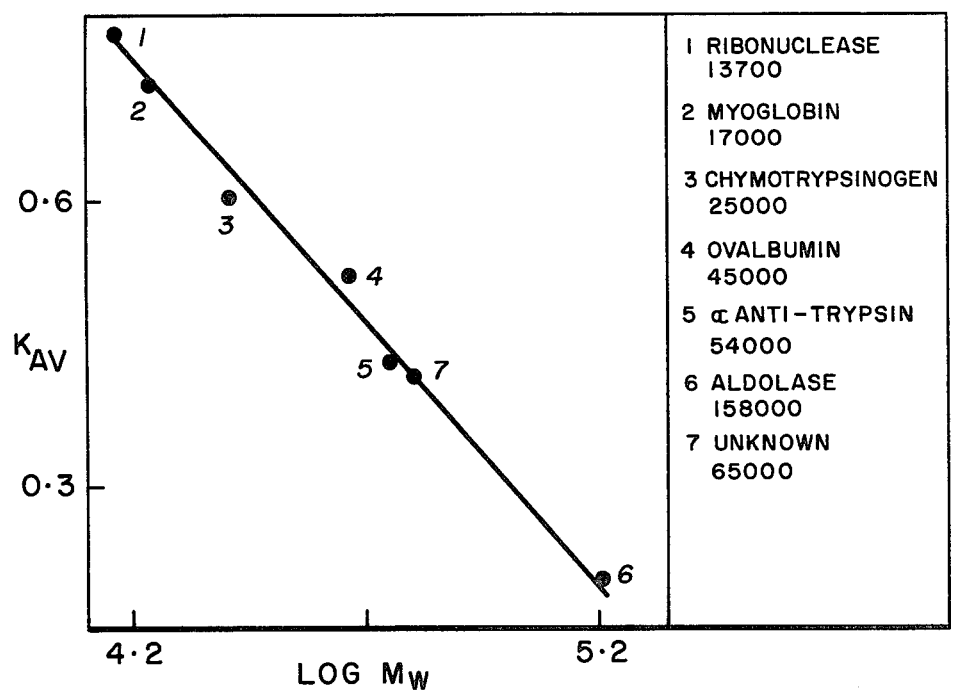

The novel high purity glycoprotein components of this invention have been characterized by amino acid composition, carbohydrate composition, molecular weight and isoelectric point in addition to the biological activity as trypsin inhibitors and inhibitors of endothelial cell growth.

(a) Amino acid composition

Samples of the two glycoprotein components (hereinafter referred to as Components A and B) were hydrolyzed in 6N HCl for 18, 30 and 48 hours and their amino acid compositions determined in duplicate in accordance with standard procedure published by Spackman and Moore, *Anal. Chem.* 30, 1190-1206 (1958).

The amion acid residues for both glycoproteins are shown in Table 1, below. Since analyses of both components showed no sulfhydryl groups with Ellman's reagent [5,5'-Dithiobis(2-nitrobenzoic acid)], it is concluded that Component A contains five disulfide bonds and Component B contains two disulfide bonds based on the cysteine composition.

TABLE 1

| | Amino Acid Composition, Residues | |
|---|---|---|
| Amino Acid | Component A | Component B |
| LYS | 25 | 19 |
| HIS | 10 | 9 |
| ARG | 13 | 12 |
| ASP | 39 | 35 |
| THR | 23 | 20 |
| SER | 31 | 24 |
| GLU | 47 | 40 |
| PRO | 28 | 23 |
| GLY | 22 | 19 |
| ALA | 34 | 28 |
| ½ CYS | 10 | 4 |
| VAL | 31 | 27 |
| MET | 5 | 4 |
| ILE | 15 | 14 |
| LEU | 37 | 35 |
| TYR | 10 | 8 |
| PHE | 16 | 15 |

The above determination for amino acid compositions should be considered to be subject to the usual error of about ±10% of the values indicated.

(b) Carbohydrate composition

Carbohydrate analyses of Components A and B were made in accordance with published standard procedures. Both Components A and B were thus found to contain hexose, fucose, sialic acid and hexosamine. Hexose was determined according to the procedure of Roe, *J. Biol. Chem.* 212, 335 (1955); fucose was determined according to the procedure of Dische and Shettles, *J. Biol. Chem.* 175, 595 (1948); sialic acid was determined according to the procedure of Spiro, *J. Biol. Chem.* 237, 646 (1962); and hexosamine was determined according to the procedure of Boas, *J. Biol. Chem.* 204, 553 (1953). Table 2, below, shows the carbohydrate content for Components A and B as thus determined.

TABLE 2

| | Carbohydrate Composition, % | |
|---|---|---|
| Carbohydrate | Component A % | Component B % |
| Hexose | 8 | 11 |

TABLE 2-continued

| | Carbohydrate Composition, % | |
|---|---|---|
| Carbohydrate | Component A % | Component B % |
| Fucose | 0.3 | 0.4 |
| Sialic Acid | 11 | 4 |
| Hexosamine | <6 | <6 |

Due to the limitations of the specific procedures used in making the above carbohydrate determinations, the inventors are not bound to the specific content set forth above.

(c) Molecular weight

The molecular weights of Components A and B were determined by two methods, namely, by SEPHADEX G-200 gel exclusion chromatography and by SDS electrophoresis.

The Sephadex G-200 used in the first of these methods is a bead-formed cross-linked dextran gel manufactured by Pharmacia Fine Chemicals AB, Uppsala, Sweden, and its composition and method of making is described in U.S. Pat. No. 3,042,667. Sephadex gel exclusion chromatography separates molecules according to size. That is, molecules larger than the largest pores in the swollen gel beads cannot enter the gel and are eluted therefrom first. Smaller molecules, which enter the gel beads to varying extent depending on their size and shape, are eluted in order of decreasing molecular size.

FIG. 1 shows the molecular weights of a series of proteins as estimated by the Sephadex G-200 gel exclusion chromatography using: a column 2.6×62 cm; eluant 2.0 M NaCl in 50 mM Tris buffer, pH 7.5; and a flow rate of 15 ml per hour. The molecular weights of Components A and B (shown as unknown) are estimated from the standard curve of the log molecular weight (log $M_w$) vs. migration index $K_{av}$) plotted for a series of proteins of known molecular weights.

In the SDS electrophoresis, the Components A and B are first solubilized with sodium dodecylsulfate (SDS) and then subjected to polyacrylamide gel electrophoresis and separated according to size by the molecular sieving effects of the gel. The migration rate correlates with the molecular weight. In this procedure, the component samples were heated at 60° C. for 30 minutes in 1% SDS, 0.3% 2-mercaptoethanol and 1 mM EDTA (ethylenediaminetetraacetic acid) before application to 7.5% polyacrylamide gels.

Figure 2:
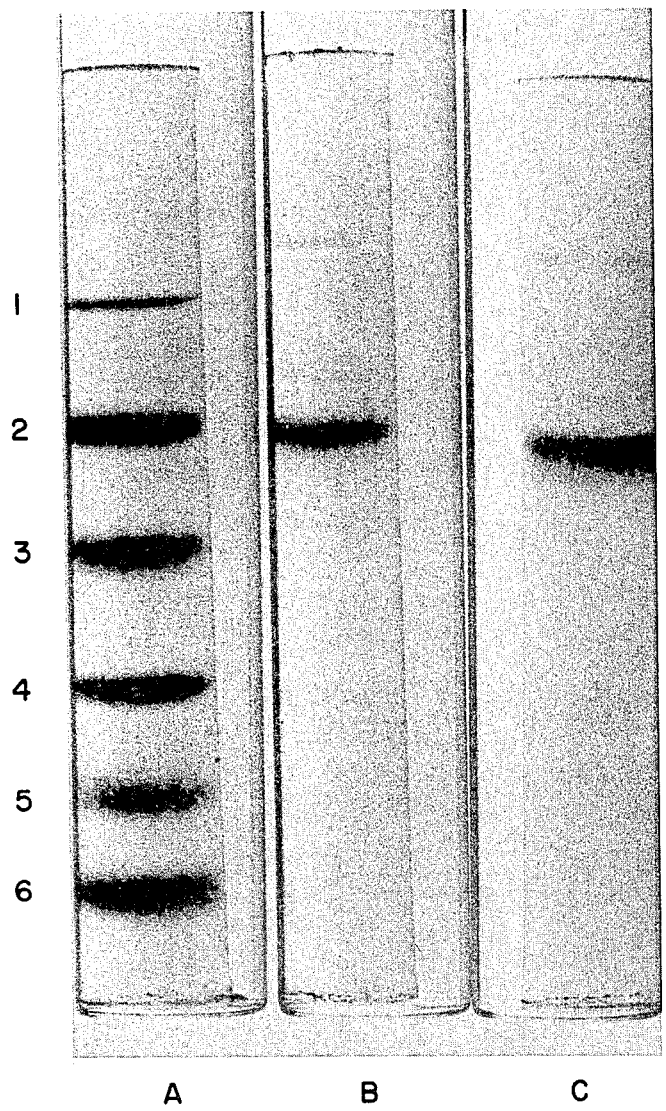

FIG. 2 shows the SDS electrophoresis pattern for a series of proteins of known molecular weights (Gel A) vs. the single band for Component A (Gel B) and the single band for Component B (Gel C). The numerals shown in FIG. 2 alongside the electrophoretic bands for Gel A refer to the following standard proteins:

| | Protein | Mol. Wt. |
|---|---|---|
| (1) | Phosphorylase b | 94,000 |
| (2) | Albumin | 67,000 |
| (3) | Ovalbumin | 43,000 |
| (4) | Carbonic Anhydrase | 30,000 |
| (5) | Soybean Trypsin Inhibitor | 20,100 |
| (6) | α-Lactalbumin | 14,000 |

Both of the foregoing methods give a molecular weight of 65,000±10,000 daltons, thereby indicating a single chain protein (d) Isoelectric point The isoelectric points of Components A and B were determined by isoelectric focusing. According to this procedure, proteins are separated according to isoelectric point by electrophoresis on a gel in which a stable pH gradient is generated, extended from a low pH at the anode to a high pH at the cathode. Each component sample was focused on a LKB Ampholine PAG plate (LKB Instruments, Inc.) at pH 3.5–9.5. Each of Components A and B focused in a zone centered at pH 3.8

The high purity glycoprotein Components A and B of this invention were isolated from an aqueous extract of bovine cartilage. Fine scraped veal cartilage was first extracted with 1.0 M guanidine.HCl, concentrated, dialyzed and lyophilized to provide a crude extract from which the glycoprotein components were then isolated by a series of separation steps.

The preferred extraction procedure is illustrated by the following example.

EXAMPLE 1

Segments of cartilage are excised from the distal tips of scapulae of calves less than two weeks old and scraped to remove any exogenous tissue. The cleaned cartilage (4000 grams) is then extracted with 40 liters of an extracting solution consisting of 1.0 M guanidine.HCl in 0.02 M sodium maleate, pH 6.0, by stirring the mixture for 23 hours, filtering through cheese cloth, centrifuging and filtering through a 0.45μ membrane. The filtrate is concentrated to 2.5 liters by Millipore ® PTGC ultrafiltration using a 10,000 Mol. Wt. cut-off filter, dialyzed against distilled water overnight (about 15 hours) and centrifuged. The resulting precipitate is discarded and the supernate is diluted to about 10 liters, filtered through a 0.45μ membrane, concentrated and desalted by Millipore PTGC ultrafiltration using a 10,000 Mol. Wt. cut-off filter. A salt-free, clear solution of about 1.5 liters is thus obtained which is sterile filtered with a 0.45μ membrane and then lyophilized to provide 23.2 grams of crude extract.

Isolation of the proteoglycan Components A and B from the above prepared extract preferably is carried out by a series of steps as follows:

(1) 40–80% Ammonium sulfate salt fractionation;

(2) Adsorption on DEAE-Sephadex in 0.01 M NaCl, 50 mM Tris buffer, pH 8.0, and subsequent elution with a linear salt gradient to 0.25 M NaCl;

(3) Passage over SP-Sephadex in 50 mM sodium acetate, pH 5.0; and (4) Passage over Con A-Sepharose in 0.5 M NaCl, 50 mM MES (4-morpholineethanesulfonic acid), pH 6.7.

The ammonium sulfate fractionation in step 1 is carried out at two concentrations, first at 40% and then at 80% with retention of the fraction soluble at 40% but insoluble at 80%.

The DEAE-Sephadex used in step 2 is a weakly basic anion exchanger having diethylaminoethyl (DEAE) functional groups and chloride counter ions. The DEAE functional group is attached by ether linkages to the glucose units in the dextran chains of the Sephadex.

SP-Sephadex used in step 3 is a strongly acidic cation exchanger having sulphopropyl functional groups and sodium counter ions.

Con A-Sepharose used in step 4 is Sepharose 4B to which concanavalin A has been coupled by the CNBr method. Sepharose is a bead-formed agarose gel and concanavalin A is a lectin isolated from the jack bean.

The preferred isolation procedure is further illustrated by the following example.

EXAMPLE 2

$(NH_4)_2SO_4$ Fractionation.

Two grams of lyophilized extract from Example 1, above, are dissolved in 100 ml of 0.2 M NaCl, 5 mM Tris pH 7.5. Twenty-four grams of solid $(NH_4)_2SO_4$ (40% of saturation) are added, the solution stirred at room temperature for 20 minutes and the resulting precipitate spun down and discarded. The supernatant is collected and made 80% of saturation in $(NH_4)_2SO_4$. (The volume usually remains about 100.0 ml so approximately 28 grams of the solid are required). The precipitate is spun down and redissolved in about 20.0 ml of water.

Exhaustive Dialysis.

The protein solution from the above fractionation step is dialyzed exhaustively vs. 3 changes of 4 liters of cold, deionized water. Any precipitate is spun down. The supernatant is then dialyzed vs. 0.10 M NaCl, 50 mM Tris pH 8.0.

DEAE-Sephadex Chromatography.

Four grams of A-50-120 DEAE-Sephadex are swollen in 0.10 M NaCl, 50 mM Tris pH 8.0. The ion exchanger is then poured into a column $(2.6 \times 30)$ giving a bed height of about 18 cm. The column is packed at room temperature at a flow rate of 45 ml/hr which is used throughout. After packing, a one centimeter layer of Sephadex G-25 coarse is poured on top of the bed surface to protect it from agitation. The sample from the above salt fractionation step is applied to the ion exchanger and the column washed with starting buffer. A protein peak washes through, but it contains no trypsin inhibition. When $A_{280}$ returns to zero, a linear salt gradient is applied which increases from 0.10 M NaCl, 50 mM Tris pH 8.0 to 0.25 M NaCl, 50 mM Tris pH 8.0. The total volume of the gradient solution is five times the bed volume. After application of the salt gradient, twenty ml fractions are collected and assayed for trypsin inhibition.

Sample Concentration.

The active fractions from the previous step are pooled and made 40% in $(NH_4)_2SO_4$. Any precipitate is removed and the supernatant made 80% in $(NH_4)_2SO_4$. The precipitate is collected, redissolved in water, dialyzed vs. 4 liters of cold water and then dialyzed vs. 1 liter of 50 mM sodium acetate pH 5.0.

SP-Sephadex Chromatography.

Two grams of SP-50-120 SP-Sephadex are swollen in 50 mM sodium acetate pH 5.0 and poured into a column $(1.5 \times 30$ cm) giving a bed height of 26 cm. The column is packed at room temperature at a flow rate of 15 ml/hr which is used throughout. After packing, the gel surface is protected by application of a one centimeter layer of Sephadex G-25 coarse. The above-concentrated sample is applied to the ion exchanger and the column washed with the starting buffer. A protein peak washes through which contains the trypsin inhibitor. Another protein peak washes off with 1.0 M NaCl, 50 mM sodium acetate pH 5.0, but it contains no trypsin inhibition. The active fractions are pooled and dialyzed vs. 1.0 M NaCl, 50 mM MES pH 6.7.

Con A-Sepharose Affinity Chromatography.

Thirty-five mls of Con A-Sepharose 4B are washed with 1.0 M NaCl, 50 mM MES pH 6.7 and poured into a $1.5 \times 30$ cm column. The column is packed and operated throughout at 10 ml/hr at room temperature. The protein solution from the previous step is pumped onto the column and fractions are collected. A protein peak, which contains trypsin inhibition (Component A) washes through. When the absorbance returns to zero, a solution of 100 mM α-methyl-D-mannoside in 1.0 M NaCl, 50 mM MES pH 6.7 is applied to the column. This displaces another protein peak which also has trypsin inhibition (Component B). Each of these peaks gives a single band on SDS disc gels.

It will be understood that the novel high purity glycoprotein Components A and B of this invention are not limited to preparation by the above specific examples which are set forth for purposes of illustration and not limitation. Other such fractionation salts, ion exchange resins, lectins, buffers and gel filtration materials can be used as will be readily apparent by analogy to the specific materials used in the foregoing examples.

The high purity glycoprotein Components A and B prepared as in Example 2, above, were shown to have useful activity as inhibitors of endothelial cell growth and as trypsin inhibitors as set forth in the following example.

EXAMPLE 3

I. Endothelial Cell Growth Inhibition:*

Bovine endothelial cells were isolated from bovine aortas, obtained from 1 to 14-day old calves. The aortic lumens were rinsed three times with lactated Ringer's solution and incubated at room temperature for 30 minutes with 4–5 ml of collagenase II (1 mg/ml) and 0.1% fetal calf serum in phosphate buffered saline. The collagenase solution was removed and replaced with Dulbecco's Modified Eagles Medium and supplemented with penicillin (50 μ/ml) and streptomycin (50 μg/ml). The endothelial cells were harvested by shaking the aortas, removing the medium and repeating this procedure three times. The pooled cells were plated in 25 $cm^2$ tissue culture flasks and grown in Dulbecco's Modified Eagles Medium and supplemented with 10% calf serum, penicillin (50 μ/ml), streptomycin (50 μg/ml) and 0.1% fibroblast growth factor. The endothelial cells were cloned using the same media. Once the cells were established, however, further growth and passage were carried out in media without fibroblast growth factor.

*Assays kindly performed by Dr. R. Langer, Children's Hospital, Harvard Medical School, Boston, Massachusetts.

To study cell growth inhibition, the wells of a 24 well Falcon plate were filled with 0.6 ml of a 1% agarose solution dissolved in Medium 199 supplemented with 10% calf serum, penicillin (50 μ/ml) and streptomycin (50 μg/ml). After solidification of the agarose, wells (2 mm in diameter) were punched out with a cork borer. These wells were filled with 10 μl of endothelial cells $(6.5 \times 10^5$ cells/ml). After the cells had adhered, an additional 0.3 ml of medium was added. After 24 hours, the agarose was removed, leaving a circle of cells in the center of the wells. Fresh media or media containing inhibitor was then added. The diameter of the circles was measured each day over a six-day period with a Nikon profile projector. The number of cells in a well under different growth conditions was found to be proportional to the diameter of the circle.

Addition of either Component A or Component B to growing endothelial cells resulted in inhibition of growth. The data indicate that Component A is the more potent inhibitor; at 300 μg/ml, growth was approximately 50% of that of the control. On the other hand, at the same concentration Component B shows 77% of the control growth.

II. Trypsin Inhibition:

Both Components A and B are strong inhibitors of trypsin. Trypsin inhibition was determined by incubating samples of Component A and Component B in trypsin for about five hours on ice in 1.0 M NaCl, 25 mM Tris buffer, pH 8.0. Assays were performed in 0.040 M Tris buffer, pH 8.1, containing 0.01 M $CaCl_2$ using 0.01 M TAME (N α-p-Tosyl-L-arginine methyl ester hydrochloride) as substrate. Titration curves of % inhibition vs. moles inhibitor/moles of trypsin show that Component A is the more potent trypsin inhibitor.

Various other examples will be apparent to the person skilled in the art after reading the present disclosure without departing from the spirit and scope of the invention. All such other examples are understood to be included within the scope of the appended claims.

What is claimed is:

1. A high purity glycoprotein isolated from bovine cartilage selected from the group consisting of Component A and Component B and having the following characteristics:

(a) amino acid composition as follows:

|  | Number of Residues | |
|---|---|---|
| Amino Acid | Component A | Component B |
| LYS | 25 | 19 |
| HIS | 10 | 9 |
| ARG | 13 | 12 |
| ASP | 39 | 35 |
| THR | 23 | 20 |
| SER | 31 | 24 |
| GLU | 47 | 40 |
| PRO | 28 | 23 |
| GLY | 22 | 19 |
| ALA | 34 | 28 |
| ½ CYS | 10 | 4 |
| VAL | 31 | 27 |
| MET | 5 | 4 |
| ILE | 15 | 14 |
| LEU | 37 | 35 |
| TYR | 10 | 8 |
| PHE | 16 | 15 | said number of residues for each amino acid being subject to a variation of about ±10% from the number stated;

(b) carbohydrate composition comprising hexose, fucose, sialic acid and hexosamine;
   (c) molecular weight of about 65,000±10,000;
   (d) isoelectric point of about 3.8; and
   (e) having activity as an inhibitor of endothelial cell growth and as a trypsin inhibitor.

2. A process of preparing the glycoproteins of claim 1 comprising the steps of
   (a) fractionating a guanadine .HCl extract of bovine cartilage with 40–80% ammonium sulfate;
   (b) adsorbing the fractionated substance with DEAE-Sephadex ion exchanger and desorbing by elution;
   (c) passing the eluate over SP-Sephadex ion exchanger;
   (d) passing over Con A-Sepharose; and
   (e) recovering the glycoproteins therefrom.

3. A process for preparing the glycoproteins of claim 1 comprising the steps of
   (a) fractionating a guanidine .HCl extract of bovine cartilage with 40–80% ammonium sulfate;
   (b) adsorbing the fractionated substance with DEAE-Sephadex ion exchanger in about 0.01 M NaCl, buffered at about pH 8.0, and desorbing by eluting with a substantially linear salt gradient to about 0.25 M NaCl;
   (c) passing the eluate over SP-Sephadex in about 50 mM sodium acetate, about pH 5.0;
   (d) passing over Con A-Sepharose in about 0.5 M NaCl, buffered at about pH 6.7; and
   (e) recovering the glycoproteins therefrom.

* * * * *

UNITED STATES PATENT AND TRADEMARK OFFICE
CERTIFICATE OF CORRECTION

PATENT NO. : 4,243,582

DATED : January 6, 1981

INVENTOR(S) : Curtis A. Spilburg and James M. Schuck

It is certified that error appears in the above—identified patent and that said Letters Patent is hereby corrected as shown below:

In Claim 3, col. 8, line 34 "0.01 M" should read --0.10 M--.

Signed and Sealed this

Twenty-first Day of July 1981

[SEAL]

Attest:

GERALD J. MOSSINGHOFF

Attesting Officer     Commissioner of Patents and Trademarks